US012782365B2

(12) United States Patent
Guo et al.

(10) Patent No.: US 12,782,365 B2
(45) Date of Patent: Nov. 3, 2026

(54) ANTIBODY COMBINATION AGAINST REGENERATING ISLET-DERIVED PROTEIN 1α, DETECTION KIT COMPRISING SAME AND METHOD OF DETECTING

(71) Applicant: SENBOLL BIOTECHNOLOGY CO., LTD., Shenzhen (CN)

(72) Inventors: Jian Guo, Shenzhen (CN); Xinying Wang, Guangzhou (CN); Yaxian Zhou, Shenzhen (CN); Desen Wan, Guangzhou (CN); Yujing Fang, Guangzhou (CN); Qingjian Ou, Guangzhou (CN); Tingting Fan, Guangzhou (CN)

(73) Assignee: Senboll Biotechnology Co., Ltd., Shenzhen (CN)

( * ) Notice: Subject to any disclaimer, the term of this patent is extended or adjusted under 35 U.S.C. 154(b) by 507 days.

(21) Appl. No.: 18/562,179

(22) PCT Filed: Jul. 4, 2022

(86) PCT No.: PCT/CN2022/103719

§ 371 (c)(1),
(2) Date: Nov. 17, 2023

(87) PCT Pub. No.: WO2023/284579

PCT Pub. Date: Jan. 19, 2023

(65) Prior Publication Data

US 2024/0241135 A1 Jul. 18, 2024

(30) Foreign Application Priority Data

Jul. 14, 2021 (CN) ........................ 202110798131.9

(51) Int. Cl.

| | |
|---|---|
| ***G01N 33/68*** | (2006.01) |
| ***C07K 16/18*** | (2006.01) |
| ***G01N 33/535*** | (2006.01) |
| ***G01N 33/57535*** | (2026.01) |

(52) U.S. Cl.

CPC ......... *G01N 33/6893* (2013.01); *C07K 16/18* (2013.01); *G01N 33/535* (2013.01); *G01N 33/57535* (2026.01); *C07K 2317/565* (2013.01); *C07K 2319/61* (2013.01); *G01N 2800/06* (2013.01)

(58) Field of Classification Search

CPC ............ G01N 33/6893; G01N 33/535; G01N 33/57535; G01N 33/5753; G01N 33/577; G01N 33/57585; G01N 2800/06; G01N 2800/062; G01N 2800/065; G01N 2800/067; G01N 2333/47; C07K 16/181; C07K 16/26; C07K 2317/565; C07K 2317/92; C07K 2317/51; C07K 2317/515; C07K 2317/56; C07K 2319/61

See application file for complete search history.

(56) References Cited

FOREIGN PATENT DOCUMENTS

| | | | |
|---|---|---|---|
| CN | 104640880 | A | 5/2015 |
| CN | 107533062 | A | 1/2018 |
| CN | 107674884 | A | 2/2018 |
| CN | 107686521 | A | 2/2018 |
| CN | 110456072 | A | 11/2019 |
| CN | 111971301 | A | 11/2020 |
| CN | 113248609 | A | 8/2021 |
| EP | 0369797 | A2 | 5/1990 |
| JP | 2010046057 | A | 3/2010 |
| WO | 2011127344 | A2 | 10/2011 |
| WO | 2018109058 | A9 | 6/2018 |

OTHER PUBLICATIONS

International Search Report and Written Opinion mailed Oct. 10, 2022 by the China National Intellectual Property Administration as International Searching Authority for counterpart international patent application No. PCT/CN2022/103719.

*Primary Examiner* — Robert S Landsman

(74) *Attorney, Agent, or Firm* — Armstrong Teasdale LLP

(57) ABSTRACT

The present invention provides an antibody combination that can be used to detect regenerating islet-derived protein 1α (REG1A), each antibody in the antibody combination can specifically bind to REG1A with high affinity so as to form a double-antibody sandwich form, thereby enabling qualitative and quantitative detection of human REG1A. The antibody combination or an ELISA detection kit comprising the antibody combination can be used for auxiliary diagnosis or disease risk prediction of REG1A-related diseases.

15 Claims, 6 Drawing Sheets

Specification includes a Sequence Listing.

ANTIBODY COMBINATION AGAINST REGENERATING ISLET-DERIVED PROTEIN 1α, DETECTION KIT COMPRISING SAME AND METHOD OF DETECTING

CROSS REFERENCE TO RELATED APPLICATIONS

This application is a U.S. national phase filing of international patent application number PCT/CN2022/103719 filed Jul. 14, 2021, that claims the right of priority to Chinese Patent Application No. CN202110798131.9 filed on Jul. 14, 2021, the entireties of which are incorporated herein by reference.

FIELD OF THE INVENTION

The present invention relates to the field of biological testing. More particularly, the present invention relates to a biological testing technology of serologic markers, in particular to an antibody combination used for the quantitative detection of regenerating islet-derived protein 1α (REG1A) in serum and a detection kit containing REG1A.

BACKGROUND OF THE INVENTION

The regenerating islet-derived protein 1α (regenerating family member 1 alpha, REG1A) is a member of regenerating gene (REG) family. The proteins of members of this family have some common structures, which mainly work in the digestive system, are closely related with the growth function of cells and may influence the growth of islet cells, nerve cells and epithelial cells. Normally, REG1A is primarily expressed in the pancreas and is also observed in the gastric mucosa and the kidneys in small amounts. REG1A is not expressed in healthy intestines, but REG1A expression will significantly rise if a lesion develops.

At present, extensive researches have been conducted into the associations between REG1A and different types of diseases. For example, researches show that human serum REG1A can be used as a clinical marker for early detection of Alzheimer's disease; in addition, it is found that this gene is clinically significant in the development and progression of malignant tumors, such as nasopharyngeal carcinoma (NPC), bladder cancer, primary liver cancer, breast cancer, and cutaneous melanoma. More researches show that REG1A correlates with the development of inflammatory diseases of the gastrointestinal system and tumors.

A double-antibody sandwich enzyme-linked immunosorbent assay (DAS-ELISA) has the following advantages: easy to operate, high-efficiency, reliable and suitable for rapid screening of a large batch of samples, and especially a monoclonal antibody-based DAS-ELISA has higher stability and specificity. Therefore, attempts can be made to develop an antibody or an antibody combination that can specifically bind to REG1A and be effectively detected, to prepare a reagent for detection or diagnosis that can be used to detect the concentration of regenerating islet-derived protein 1α in serum qualitatively or quantitatively.

DESCRIPTION OF THE INVENTION

To solve the technical problems, the present invention is to provide a new reagent and method that can be used to detect the existence or concentration of REG1A in serum with high sensitivity and specificity.

More particularly, the present invention is to provide an antibody combination targeting different epitopes on regenerating islet-derived protein 1α (REG1A). Each antibody in this combination needs to bind to REG1A with high affinity and specificity and form a double-antibody sandwich form to qualitatively or quantitatively detect human REG1A.

Based on the antibody combination, another object of the present invention is to provide an ELISA kit containing the antibody combination; for example, a DAS-ELISA kit is used for qualitative and quantitative detection of REG1A in the samples to be tested.

The technical scheme of the present invention is as follows.

In one aspect, the prevent invention provides an antibody combination, and the antibody combination includes:

(i) Antibody 1: The Antibody 1 consists of heavy chains (HC) and light chains (LC), wherein the heavy chains include a heavy chain CDR1 (H-CDR1) illustrated in SEQ ID NO. 1, a heavy chain CDR2 (H-CDR2) illustrated in SEQ ID NO. 2 and a heavy chain CDR3 (H-CDR3) illustrated in SEQ ID NO. 3 and the light chains include a light chain CDR1 (L-CDR1) illustrated in SEQ ID NO. 6, a light chain CDR2 (L-CDR2) illustrated in SEQ ID NO. 7 and a light chain CDR3 (L-CDR3) illustrated in SEQ ID NO. 8; and (ii) Antibody 2: The Antibody 2 consists of heavy chains (HC) and light chains (LC), wherein the heavy chains include a heavy chain CDR1 (H-CDR1) illustrated in SEQ ID NO. 11, a heavy chain CDR2 (H-CDR2) illustrated in SEQ ID NO. 12 and a heavy chain CDR3 (H-CDR3) illustrated in SEQ ID NO. 13 and the light chains include a light chain CDR1 (L-CDR1) illustrated in SEQ ID NO. 16, a light chain CDR2 (L-CDR2) illustrated in SEQ ID NO. 17 and a light chain CDR3 (L-CDR3) illustrated in SEQ ID NO. 18.

In the context of the present invention, the Antibody 1 and the Antibody 2 are the binding agents that can specifically bind the regenerating islet-derived protein 1α (REG1A).

Preferably, the heavy chains of the Antibody 1 include a heavy chain variable region (VH), the light chains include a light chain variable region (VL), and the VH of the Antibody 1 includes an amino acid sequence illustrated in SEQ ID NO. 4 and the VL includes an amino acid sequence illustrated in SEQ ID NO. 9; and/or, the heavy chains of the Antibody 2 include a heavy chain variable region (VH), the light chains include a light chain variable region (VL), and the VH of the Antibody 2 includes an amino acid sequence illustrated in SEQ ID NO. 14 and the VL includes an amino acid sequence illustrated in SEQ ID NO. 19.

Preferably, the Antibody 1 and the Antibody 2 are selected from mouse, chimeric and humanized antibodies. Preferably, the Antibody 1 and the Antibody 2 are selected from monoclonal, Fab, Fv and ScFv antibodies, etc.

Preferably, in the antibody combination provided in the present invention, the Antibody 1 and/or the Antibody 2 is a monoclonal antibody, consisting of 2 heavy chains and 2 light chains, and a mouse IgG1/Kappa isotype is preferred. In this aspect, the antibody structure is schematically illustrated in FIG. 1.

According to the Detailed Description of the Preferred Embodiments of the present invention, the heavy chains of the Antibody 1 include an amino acid sequence illustrated in SEQ ID NO. 5 and the light chains include an amino acid sequence illustrated in SEQ ID NO. 10; and/or, the heavy chains of the Antibody 2 include an amino acid sequence illustrated in SEQ ID NO. 15 and the light chains include an amino acid sequence illustrated in SEQ ID NO. 20.

According to the Detailed Description of the Preferred Embodiments of the present invention, the Antibody 1 and/or the Antibody 2 has a detectable label. Preferably, the Antibody 2 has a detectable label. The detectable label includes enzyme label, radioactive label, luminescent label, color rendering label, hapten (e.g. digoxin and biotin), metal complex or metal (e.g. colloidal gold).

In a further aspect, the present invention provides a use of the antibody combination to prepare a reagent for detecting the regenerating islet-derived protein 1α (REG1A). Alternatively, the present invention provides a use of the antibody combination to prepare a reagent for auxiliary diagnosis or disease risk prediction of REG1A-related diseases. Preferably, in the context of the present invention, the regenerating islet-derived protein 1α (REG1A) is a human regenerating islet-derived protein 1α (NCBI reference sequence: NP_002900.2).

In the context of the present invention, REG1A expression rises in the REG1A-related diseases. Preferably, the REG1A-related diseases are diseases of the digestive system. Preferably, the diseases are diseases of the digestive tract, such as inflammatory bowel disease (IBD), peptic ulcer, adenomatous polyp, Stage 1, Stage 2, Stage 3 or Stage 4 colorectal cancer, gastroenteritis or gastric cancer. Alternatively, the diseases are pancreatitides, such as acute pancreatitis.

In the context of the present invention, the reagent may be a reagent that can be used to detect the existence or concentration of REG1A in the biological samples from subjects. In the context of the present invention, "concentration" refers to the amount of the protein that can be detected in a biological sample, and "concentration" and "level" or "amount" can be used interchangeably herein. According to the Detailed Description of the Preferred Embodiments of the present invention, the existence or concentration of REG1A can be detected in whole blood, serum or plasma.

The detection results can be used to help diagnose whether the subjects suffer from any of the REG1A-related diseases or to predict whether the subjects are at risk of suffering from any of the REG1A-related diseases. In the context of the present invention, the subjects are mammals, preferably primates and more preferably humans. The biological samples are taken from one or more of the whole blood, plasma, serum, blood cell, ascites, lymph fluid, saliva, phlegm, perspiration, urine, mucus, interstitial fluid, tissue biopsy and cells from subjects, preferably whole blood, serum or plasma.

Preferably, the reagent can be used in the following detection methods: chemiluminescence immunoassay, immunonephelometry, enzyme-linked immunosorbent assay (ELISA), Western blotting, antibody microarray, immunoprecipitation, radioimmunoassay (RIA), etc. Preferably, the reagent is a detection reagent used for an ELISA, such as the detection reagent for a DAS-ELISA, wherein the ELISA is used to detect the regenerating islet-derived protein 1α (REG1A) in whole blood, serum or plasma. Preferably, in the ELISA, the Antibody 1 is used as a capture antibody (coated antibody) and the Antibody 2 is used as a detection antibody.

In still a further aspect, the present invention also provides a kit, and the kit contains the antibody combination in the present invention.

The kit is used to detect the existence or concentration of REG1A in biological samples from subjects, so it can be used for auxiliary diagnosis or disease risk prediction of REG1A-related diseases. Preferably, the regenerating islet-derived protein 1α (REG1A) is a human regenerating islet-derived protein 1a. The subjects are mammals, preferably primates and more preferably humans. The biological samples are taken from one or more of the whole blood, plasma, serum, blood cell, ascites, lymph fluid, saliva, phlegm, perspiration, urine, mucus, interstitial fluid, tissue biopsy and cells from subjects, preferably whole blood, serum or plasma. REG1A expression rises in the REG1A-related diseases. Preferably, the REG1A-related diseases are diseases of the digestive system. Preferably, the diseases are diseases of the digestive tract, such as inflammatory bowel disease (IBD), peptic ulcer, adenomatous polyp, Stage 1, Stage 2, Stage 3 or Stage 4 colorectal cancer, gastroenteritis or gastric cancer. Alternatively, the diseases are pancreatitides, such as acute pancreatitis.

The kit can be used in the following detection methods: chemiluminescence immunoassay, immunonephelometry, enzyme-linked immunosorbent assay (ELISA), Western blotting, antibody microarray, immunoprecipitation, radioimmunoassay (RIA), etc. Preferably, the kit is an ELISA kit, such as DAS-ELISA kit, and the kit includes the antibody combination provided in the present invention. Preferably, the ELISA kit includes the Antibody 1 that is used as a capture antibody and the Antibody 2 that is used a detection antibody. Preferably, the Antibody 2 has a detectable label. The detectable label includes enzyme label, radioactive label, luminescent label, color rendering label, hapten (e.g. digoxin and biotin), metal complex or metal (e.g. colloidal gold).

More preferably, the kit also includes other reagents necessary for using ELISA to detect the existence or concentration of REG1A in biological samples. For example, the kit also includes one or more of the following items or all of the following items: REG1A calibrator and/or control material, antibody diluent, wash buffer, blocking buffer, diluent of the detected sample, ELISA plate, color-developing solution and stop buffer.

In one aspect, the present invention provides a method for detecting the regenerating islet-derived protein 1α (REG1A) in the biological samples taken from subjects, and the method includes: using the antibody combination or the kit provided in the present invention to detect the existence or concentration of REG1A in the biological samples from subjects.

Alternatively, the present invention provides a method for auxiliary diagnosis or disease risk prediction of REG1A-related diseases, and the method includes: using the antibody combination or the kit provided in the present invention to detect the concentration of REG1A in the biological samples from subjects. Additionally, the method includes: comparing the detected concentration of REG1A with a reference level, and a higher concentration of REG1A in the biological samples indicates that the subjects suffer from a REG1A-related disease or are at risk of suffering from a REG1A-related disease.

In this aspect, regenerating islet-derived protein 1a, REG1A-related diseases, subjects, biological samples, detection methods, etc. are defined above.

In the method provided in the present invention, the reference level refers to the value that is determined by comprehensively considering the ROC analysis and clinical needs of healthy population and patients in terms of the concentration of regenerating islet-derived protein 1α (REG1A) in the biological samples. According to the Detailed Description of the Preferred Embodiments of the present invention, the biological samples are serum, with the reference level of 60 ng/ml.

According to the Detailed Description of the Preferred Embodiments of the present invention, the method uses the ELISA kit provided by the present invention, such as a DAS-ELISA kit. According to the Detailed Description of the Preferred Embodiments of the present invention, the following steps can be included:

(1) To coat a capture antibody (Antibody 1) on a ELISA plate and block it;
(2) To dilute the sample to be detected;
(3) To separately add the sample to be detected to different wells on the ELISA plate, optionally add a calibrator and/or a control material, add a labelled detection antibody (Antibody 2), and incubate it;
(4) To wash the plate;
(5) To detect the label on the detection antibody, such as color developing;
(6) To stop the reaction;
(7) To read the results, such as OD value; and
(8) To use the calibrator concentration as the x-axis and use the detection results (e.g. OD value) as the y-axis to draw a standard curve, and then calculate the concentration of REG1A in samples based on the detection results of the samples to be detected.

More particularly, the present invention provides an antibody combination targeting the human regenerating islet-derived protein 1α (REG1A). Each antibody in this combination can bind to REG1A with high affinity and specificity and bind to different epitopes of this protein, to form a double-antibody sandwich form to detect REG1A qualitatively or quantitatively in a combination. Correspondingly, the present invention also provides an ELISA method of using this antibody combination and its corresponding detection kit.

At present, clinical diagnosis of digestive system diseases is still dominated by pathological diagnosis. For example, the carcinoembryonic antigen (CEA) and carbohydrate antigen 19-9 (CA19-9) known in the art can be used as the biomarkers for colorectal cancer and the carbohydrate antigen 72-4 (CA72-4) can be used as the biomarker for gastric cancer, but the definitive diagnosis of colorectal cancer and gastric cancer still needs to rely on colonoscopy, enteroscopy, gastroscopy, ultrasonography, imaging and pathological examination.

Through a lot of preliminary researches, the inventor of the present invention finds that this protein, REG1A, correlates with multiple diseases of the digestive system, such as colorectal cancer, adenomatous polyp, gastric cancer, IBD, and peptic ulcer, so accurate detection can be realized according to the level of REG1A in the biological samples for auxiliary diagnosis or disease risk predication of these diseases. In this aspect, experiments have proven that the pairing of Antibody 1 (capture antibody) and Antibody 2 (detection antibody) provided in the present invention can qualitatively or quantitatively detect the human REG1A in serum with high accuracy and specificity. Particularly, compared with other antibody combinations, the optimal range of linearity of the human REG1A detected exceeds 1,000 pg/mL in case of a combination of Antibody 1 and Antibody 2 provided in the present invention, and after human serum is diluted, the concentration of REG1A in serum can be effectively determined, and for a sample with an extremely high or low concentration, the sample dilution can be adjusted to ensure the accuracy of measurement results, so the requirements for accurately detecting the level of REG1A in samples can be fully met.

The inventor of the present invention has used a lot of serum samples taken from the patients with IBD, peptic ulcer, adenomatous polyp, Stage 1~ Stage 4 colorectal cancer, gastroenteritis, gastric cancer and acute pancreatitis for verification. The results show that if the antibody combination provided by the present invention is used in DAS-ELISA, the total sensitivity of detection of serum samples from patients can reach 75%, with the maximum value of 100%, and the detection results are very accurate; and for the serum samples taken before and after the effective treatment of REG1A-related diseases, the antibody combination provided in the present invention can be used to accurately detect the concentration of REG1A in serum samples and effectively monitor the changes in the concentration of REG1A in serum.

Thus, it is proved that the antibody combination and the ELISA (e.g. DAS-ELISA) method and kit based on this combination in the present invention have a good clinical application value. For example, the antibody combination, detection method and kit provided in the present invention can help doctors judge whether a disease is a functional lesion (e.g. flatulence and diarrhea) or an organic lesion (e.g. polyp, adenoma, gastrointestinal cancer, gastric ulcer, and IBD, which need to be further confirmed with gastrointestinal endoscopy); the same can be used for companion diagnostics/prognostic monitoring of REG1A-related diseases, with the aim to help diagnose whether the therapeutic drugs of patients are effective and repeated colonoscopies can be avoided; and the same can also be used to screen the gastrointestinal organic lesions of healthy population (e.g. gastric cancer and colorectal cancer).

DESCRIPTION OF FIGURES

Combined with drawings, the embodiments provided in the present invention are explained in detail hereunder, wherein.

DETAILED DESCRIPTION OF THE PREFERRED EMBODIMENTS

Figure 1:
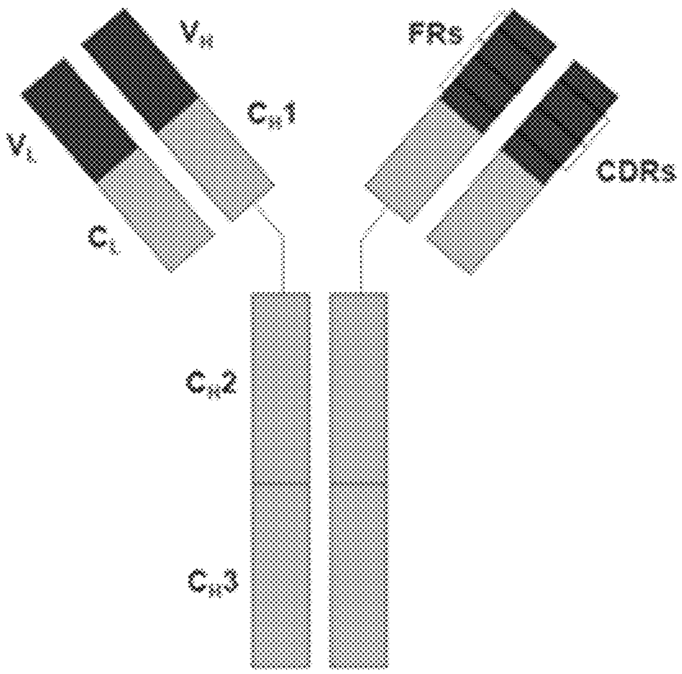
FIG. 1 is a schematic diagram of the structure of an antibody in the combination provided in the present invention when the antibody is a monoclonal antibody.

The present invention is described by reference to the preferred embodiments. Those skilled in the art can understand that these embodiments are intended to illustrate the present invention and not to limit the range of the present invention in any way.

The experiment methods in the following embodiments are conventional methods unless otherwise specified. Raw materials and reagent materials used in the following embodiments are commercially available off-the-shelf (COTS) items unless otherwise specified.

The recombinant human REG1A is recombined and prepared according to NCBI reference sequence (NP_002900.2).

Embodiment 1 Acquisition of a Monoclonal Antibody for the Human Regenerating Islet-Derived Protein 1α (REG1A)

Immunization: Mice are immunized by giving them a multipoint subcutaneous injection of a recombinant human REG1A, and this step is repeated for 3-4 times. After immunization, a small amount of blood is taken from these mice for potency assay and the spleens of mice with high potency are selected for further fusion.

Cell fusion: Splenocytes from mice are selected, grinded, and screened through a cell strainer, and then are centrifuged and washed with a culture solution. In this way, splenic lymphocyte suspension is obtained. After that, myeloma cells and splenocytes are mixed proportionally, and a fusion agent is added to the mixture for fusion.

Screening: A HAT selection culture solution is used for culturing, to screen out hybridoma cells, and meanwhile, the supernatant is measured and cultured with ELISA, to screen out the hybridoma cells producing antibodies that can be used to specifically recognize the human REG1A. Then, the screened positive hybridoma cells are cloned with the limiting dilution method to get stable monoclonal hybridoma cells.

Antibody production: The selected hybridoma cells are taken for expanded culture, the cultured supernatant is taken and purified with affinity chromatography to get monoclonal antibodies.

A total of 5 monoclonal antibodies are obtained and are mouse IgG1/Kappa isotypes after examination, which are separately named in the present invention: antibody 4H8F1; antibody 12F12A10; antibody 11D11B11; antibody 21B11D2; and antibody 25F3C4. The antibody sequence is as follows:

(i) 4H8F1:

Heavy chain (SEQ ID NO. 5 (removing signal peptide); wherein, the heavy chain variable region is SEQ ID NO. 4; CDRs are SEQ ID NO. 1/SEQ ID NO. 2/SEQ ID NO. 3 in order):

MGRLTSSFLLLIVPAYVLS*QVTLKESGPGILQPSQTLSLTCSFSG*

*FSLSTSGMSVGWIRQPSGKGLEWLAHIWWNDDKFYNPALKSRLTI*

*SKDTSKNQIFLKIASVVTADSATYYCARIEEGWFAYWGQGTLVTV*

*ST*AKTTPPSVYPLAPGSAAQTNSMVTLGCLVKGYFPEPVTVTWNS

GSLSSGVHTFPAVLQSDLYTLSSSVTVPSSTWPSETVTCNVAHPA

SSTKVDKKIVPRDCGCKPCICTVPEVSSVFIFPPKPKDVLTITLT

PKVTCVVVDISKDDPEVQFSWFVDDVEVHTAQTQPREEQFNSTFR

SVSELPIMHQDWLNGKEFKCRVNSAAFPAPIEKTISKTKGRPKAP

QVYTIPPPKEQMAKDKVSLTCMITDFFPEDITVEWQWNGQPAENY

KNTQPIMDTDGSYFVYSKLNVQKSNWEAGNTFTCSVLHEGLHNHH

TEKSLSHSPGK

Light chain (SEQ ID NO. 10 (removing signal peptide); wherein, the light chain variable region is SEQ ID NO. 9, CDRs are SEQ ID NO. 6/SEQ ID NO. 7/SEQ ID NO. 8 in order):

MKSQTQVFVFLLLCVSAAHG*SIVMTQTPKFLLVSVGDRVTITCKA*

*SQTMSNDVAWYQQKPGQSPKLLIYYASNRYTGVPDRFTGSGYGTD*

*FTFTISTVQAEDLAVYFCQQDYSSPLTFGAGTKLELK*RADAAPTV

SIFPPSSEQLTSGGASVVCFLNNFYPKDINVKWKIDGSERQNGVL

NSWTDQDSKDSTYSMSSTLTLTKDEYERHNSYTCEATHKTSTSPI

VKSFNRNEC (ii) 12F12A10:

Heavy chain (SEQ ID NO. 15 (removing signal peptide); wherein, the heavy chain variable region is SEQ ID NO. 14; CDRs are SEQ ID NO. 11/SEQ ID NO. 12/SEQ ID NO. 13 in order):

MERHWIFLFLLSITAGVHS*QVQLQQSATELARPGASVKMSCKASG*

*YTFTSYMMHWVKQRPGQGLEWIGYINPSSGYTDYNQKFKDKTTLT*

*ADKSSSTAYMQLSSLTSEDSAVYYCARYRYPHYFDYWGQGTTLTV*

*SS*AKTTPPSVYPLAPGSAAQTNSMVTLGCLVKGYFPEPVTVTWNS

GSLSSGVHTFPAVLQSDLYTLSSSVTVPSSTWPSETVTCNVAHPA

SSTKVDKKIVPRDCGCKPCICTVPEVSSVFIFPPKPKDVLTITLT

PKVTCVVVDISKDDPEVQFSWFVDDVEVHTAQTQPREEQFNSTFR

SVSELPIMHQDWLNGKEFKCRVNSAAFPAPIEKTISKTKGRPKAP

QVYTIPPPKEQMAKDKVSLTCMITDFFPEDITVEWQWNGQPAENY

KNTQPIMDTDGSYFVYSKLNVQKSNWEAGNTFTCSVLHEGLHNHH

TEKSLSHSPGK

Light chain (SEQ ID NO. 20 (removing signal peptide); wherein, the light chain variable region is SEQ ID NO. 19; CDRs are SEQ ID NO. 16/SEQ ID NO. 17/SEQ ID NO. 18 in order):

MDFQVQIFSFLLISASVIISRG*QIVLTQSPAIMSASPGEKVTMTC*

*SASSSVSYIHWYQQKSGTSPKRWIYDTSKLASGVPARFSGSGSGT*

*SYSLTISSMEAEDAAIYYCQQWS*SNPPT*FGAGTKLELK*RADAAPT

VSIFPPSSEQLTSGGASVVCFLNNFYPKDINVKWKIDGSERQNGV

LNSWTDQDSKDSTYSMSSTLTLTKDEYERHNSYTCEATHKTSTSP

IVKSFNRNEC (iii) Antibody 11D11B11:

Heavy chain (SEQ ID NO. 21 (removing signal peptide)):

MSSEHRPLTMNFGLRLIFLVLTLKGVQC*DVKLVESGGGLVKPGGS*

*LKLSCAASGFTFSSFSMSWFRQTPDKRLEWVATISSGGSSTYYPD*

*SVKGRFTISRDNAKNTLYLQMTSLKSEDTAIFYCRGGYYGNYDPL*

*DYWGQGTSVTVSA*AKTTAPSVYPLAPVCGDTTGSSVTLGCLVKGY

FPEPVTLTWNSGSLSSGVHTFPAVLQSDLYTLSSSVTVTSSTWPS

QSITCNVAHPASSTKVDKKIEPRGPTIKPCPPCKCPAPNLLGGPS

VFIFPPKIKDVLMISLSPIVTCVVVDVSEDDPDVQISWFVNNVEV

HTAQTQTHREDYNSTLRVVSALPIQHQDWMSGKEFKCKVNNKDLP

APIERTISKPKGSVRAPQVYVLPPPEEEMTKKQVTLTCMVTDFMP

EDIYVEWTNNGKTELNYKNTEPVLDSDGSYFMYSKLRVEKKNWVE

RNSYSCSVVHEGLHNHHTTKSFSRTPGK

Light chain (SEQ ID NO. 22 (removing signal peptide)):

MGIKMESQTQVFVYMLLWLSGVDG*DIVMIQSQKFMSTSVGDRVSI*

*TCTASHNVDSNVAWYQQKPGQSPQALIYSASYRYSGVPDRFTGSG*

*SGTDFTLTINNVQSEDLAEYFCQQYNSYPLT*FGGGTRLEIKRADA

APTVSIFPPSSEQLTSGGASVVCFLNNFYPKDINVKWKIDGSERQ

NGVLNSWTDQDSKDSTYSMSSTLTLTKDEYERHNSYTCEATH

KTSTSPIVKSFNRNEC (iv) Antibody 21B11D2:

Heavy chain (SEQ ID NO. 23 (removing signal peptide)):

MEWSWVFLFLLSVIAGVQS*QAQLQQSGAELVRPGASVTLSCKASG*

*YIFTDYEMHWVKQTPVHGLEWIGAIDPETGGTAYNQKFKGKARLT*

*ADKSSSTAYMELRSLTSEDSAVYYCTIYYTNHFDYWGQGTTLTVS*

*S*AKTTPPSVYPLAPGCGDTTGSSVTLGCLVKGYFPESVTVTWNSG

SLSSSVHTFPALLQSGLYTMSSSVTVPSSTWPSQTVTCSVAHPAS

STTVDKKLEPSGPISTINPCPPCKECHKCPAPNLEGGPSVFIFPP

NIKDVLMISLTPKVTCVVVDVSEDDPDVRISWFVNNVEVHTAQTQ

THREDYNSTIRVVSALPIQHQDWMSGKEFKCKVNNKDLPSPIERT

-continued

ISKIKGLVRAPQVYILPPPAEQLSRKDVSLTCLVVGFNPGDISVE

WTSNGHTEENYKDTAPVLDSDGSYFIYSKLDIKTSKWEKTDSFSC

NVRHEGLKNYYLKKTISRSPGK

Light chain (SEQ ID NO. 24 (removing signal peptide)):

MKLPVRLLVLMFWIPASSS*DVVMTQTPLSLPVSLGDQASISCRSS*

*QSLVYSNGDTYLYWYLQKPGQSPKLLIYKVSNRFSGVPDRFSGSG*

*SGTDFTLKISRVEAEDLGVYFCSQSTHVPLTFGAGTKLELK*RADA

APTVSIFPPSSEQLTSGGASVVCFLNNFYPKDINVKWKIDGSERQ

NGVLNSWTDQDSKDSTYSMSSTLTLTKDEYERHNSYTCEATHKTS

TSPIVKSFNRNEC (v) Antibody 25F3C4

Heavy chain (SEQ ID NO. 25 (removing signal peptide)):

MEWSWVFLFLLAVIAGVQS*QVQLQQSGAELVRPGASVTLSCKASG*

*YTFTDYEVHWVKQTPVHGLEWIGAIDPETGGTAYNLKFKGKAILT*

*ADKSSSTAYMELRSLTSEDSAVYYFTIYYTNNFDYWGQGTALTVS*

*S*AKTTPPSVYPLAPGCGDTTGSSVTLGCLVKGYFPESVTVTWNSG

SLSSSVHTFPALLQSGLYTMSSSVTVPSSTWPSQTVTCSVAHPAS

STTVDKKLEPSGPISTINPCPPCKECHKCPAPNLEGGPSVFIFPP

NIKDVLMISLTPKVTCVVVDVSEDDPDVRISWFVNNVEVHTAQTQ

THREDYNSTIRVVSALPIQHQDWMSGKEFKCKVNNKDLPSPIERT

ISKIKGLVRAPQVYILPPPAEQLSRKDVSLTCLVVGFNPGDISVE

WTSNGHTEENYKDTAPVLDSDGSYFIYSKLDIKTSKWEKTDSFSC

NVRHEGLKNYYLKKTISRSPGK

Light chain (SEQ ID NO. 26 (removing signal peptide)):

MKLPVRLLVLMFWIPASSS*DVVMTQTPLSLPVSLGDQASISCRSS*

*QSLVYSDGNTYLHWYLQKPGQSPKLLIYKVSYRFSGVPDRFSGSG*

*SGTDFTLKISRVEAEDLGVYFCSQSTHVPLTFGAGTKLELK*RAD

AAPTVSIFPPSSEQLTSGGASVVCFLNNFYPKDINVKWKIDGSER

QNGVLNSWTDQDSKDSTYSMSSTLTLTKDEYERHNSYTCEATHKT

STSPIVKSFNRNEC

In the sequences above, the part in bold refers to a signal peptide; the part in italic type refers to a variable region, wherein the underlined part denotes a CDR; and the underlined part behind the variable region is a constant region.

Embodiment 2 Screening and Verification of Capture and Detection Antibodies (I) First Pairing and Screening For the 5 monoclonal antibodies obtained in Embodiment 1, one antibody is paired with another as capture and detection antibodies, respectively, and the detection effect on the recombinant human REG1A of antigens is measured. The process is as follows:

Coating: A diluent (10 mM pH 7.4 PBS) is used to dilute the capture antibody to 2.5 μg/mL as a coating buffer, and the coating buffer is then added to the wells on an ELISA plate (100 μL per well) to be incubated overnight at 4° C. After that, the liquid is removed from wells, and the plate is washed twice with a wash buffer (10 mM pH7.4 PBS+0.5% TWEEN® 20 (polysorbate 20), PBST);

Blocking: A blocking buffer (10 mM pH7.4 PBS+1% BSA+0.5% TWEEN® 20) is added to the wells on an ELISA plate (250 μL per well) to be incubated for 2 h at 37° C. Then, the liquid is removed from wells, and the plate is washed twice with PBST;

Antigen incubation: A basic diluent (10 mM pH7.4 PBS+0.5% BSA+0.5% TWEEN® 20) is used to prepare the recombinant REG1A into solutions of different concentrations, and then the solutions are added to the wells of an ELISA plate (100 μL per well) to be incubated for 1 h at 37° C. After that, the liquid is removed from wells, and the plate is washed 3 times with PBST;

Detection antibody incubation: A basic diluent is used to dilute the biotin-labeled detection antibody to 1 μg/mL, and then the solution is added to the wells of an ELISA plate (100 μL per well) to be incubated for 1 h at 37° ° C. After that, the liquid is removed from wells, and the plate is washed 3 times with PBST;

Secondary antibody incubation: A basic diluent is used to dilute the HRP-labeled streptavidin (SIGMA) by a factor of 20,000, and then the solution is added to the wells of an ELISA plate (100 μL per well) to be incubated for 45 min at 37° C. After that, the liquid is removed from wells, and the plate is washed 3 times with PBST;

Color developing: A TMB substrate solution (produced by Huzhou InnoReagents Co., Ltd.) is added to the wells of an ELISA plate (100 μL per well) for color development for 15 min at 37° C. away from light. Then, a 50 μL stop buffer (0.2M sulfuric acid) is added to stop the reaction;

Reading: A microplate reader is used to measure the OD value of each well at the dominant wavelength of 450 nm and the sub-wavelength of 620/630 nm (the OD value at the dominant wavelength of 450 nm minus the OD value at the sub-wavelength of 620/630 nm).

The results are shown in Table 1.

TABLE 1

Results of the First Pairing Experiment (OD Value)

| Capture antibody (2.5 μg/mL) | Antigen (ng/mL) 100.00 | 33.33 | 11.11 | 3.70 | 1.23 | 0 | Detection antibody (1 μg/mL) |
|---|---|---|---|---|---|---|---|
| 4H8F1 | 0.09 | 0.081 | 0.081 | 0.079 | 0.074 | 0.074 | 4H8F1-biotin |
| | 4.242 | 4.223 | 4.104 | 3.736 | 2.465 | 0.21 | 11D11B11-biotin |
| | 4.33 | 4.33 | 4.217 | 3.841 | 2.987 | 0.088 | 12F12A10-biotin |
| | 0.08 | 0.073 | 0.07 | 0.068 | 0.072 | 0.069 | 21B11D2-biotin |
| | 0.101 | 0.097 | 0.095 | 0.09 | 0.09 | 0.093 | 25F3C4-biotin |
| 11D11B11 | 4.235 | 4.478 | 3.872 | 2.865 | 1.373 | 1.208 | 4H8F1-biotin |
| | 0.064 | 0.064 | 0.072 | 0.066 | 0.066 | 0.079 | 11D11B11-biotin |
| | 4.216 | 4.083 | 3.896 | 2.811 | 1.047 | 0.083 | 12F12A10-biotin |
| | 0.065 | 0.063 | 0.066 | 0.06 | 0.07 | 0.068 | 21B11D2-biotin |
| | 0.083 | 0.083 | 0.076 | 0.077 | 0.073 | 0.077 | 25F3C4-biotin |
| 12F12A10 | 3.183 | 3.267 | 3.05 | 2.425 | 1.297 | 0.068 | 4H8F1-biotin |
| | 3.153 | 3.028 | 2.688 | 1.543 | 0.934 | 0.075 | 11D11B11-biotin |
| | 0.096 | 0.098 | 0.088 | 0.088 | 0.098 | 0.089 | 12F12A10-biotin |
| | 3.352 | 3.21 | 2.892 | 2.384 | 1.177 | 0.068 | 21B11D2-biotin |
| | 3.77 | 3.759 | 3.506 | 2.998 | 1.608 | 0.085 | 25F3C4-biotin |
| 21B11D2 | 0.084 | 0.078 | 0.073 | 0.077 | 0.078 | 0.075 | 4H8F1-biotin |
| | 0.075 | 0.077 | 0.077 | 0.069 | 0.089 | 0.074 | 11D11B11-biotin |
| | 4.648 | 4.587 | 4.228 | 4.589 | 3.898 | 0.09 | 12F12A10-biotin |
| | 0.068 | 0.071 | 0.069 | 0.069 | 0.066 | 0.073 | 21B11D2-biotin |
| | 0.106 | 0.094 | 0.111 | 0.089 | 0.087 | 0.09 | 25F3C4-biotin |
| 25F3C4 | 0.086 | 0.085 | 0.078 | 0.082 | 0.087 | 0.076 | 4H8F1-biotin |
| | 0.089 | 0.083 | 0.079 | 0.076 | 0.071 | 0.074 | 11D11B11-biotin |
| | 4.476 | 4.289 | 4.373 | 4.251 | 3.764 | 0.093 | 12F12A10-biotin |
| | 0.073 | 0.071 | 0.069 | 0.068 | 0.066 | 0.068 | 21B11D2-biotin |
| | 0.107 | 0.118 | 0.103 | 0.102 | 0.099 | 0.093 | 25F3C4-biotin |

According to Table 1, compared with other sets of paired antibodies, the following three sets of paired antibodies can obtain a better detection effect: separately used as 4H8F1, 21B11D2 and 25F3C4 of the capture antibody and as 12F12A10 of the detection antibody.

(II) Second Pairing and Screening

The three sets of paired antibodies obtained from the first pairing and screening are further screened. The process is as follows:

Coating: A PBS is used to dilute the capture antibody to 1 μg/mL as a coating buffer, and then the coating buffer is added to the wells on an ELISA plate (100 μL per well) to be incubated overnight at 4° C. After that, the liquid is removed from wells, and the plate is washed twice with PBST;

Blocking: A blocking buffer is added to the wells on an ELISA plate (250 μL per well) to be incubated for 2 h at 37° C. After that, the liquid is removed from wells, and the plate is washed twice with PBST;

Antigen incubation: A basic diluent is used to prepare the recombinant REG1A into solutions of different concentrations, and then the solutions are added to the wells of an ELISA plate (100 μL per well) to be incubated for 1 h at 37° C. After that, the liquid is removed from wells, and the plate is washed 3 times with PBST;

Detection antibody incubation: A basic diluent is used to dilute the HRP-labeled detection antibody by a factor of 30,000, and then the solution is added to the wells of an ELISA plate (100 μL per well) to be incubated for 1 h at 37° C. After that, the liquid is removed from wells, and the plate is washed 3 times with PBST;

Color developing: A TMB substrate solution is added to the wells of an ELISA plate (100 μL per well) for color development for 15 min at 37° C. away from light. Then, a 50 μL stop buffer (0.2M sulfuric acid) is added to stop the reaction;

Reading: A microplate reader is used to measure the OD value of each well at the dominant wavelength of 450 nm and the sub-wavelength of 620/630 nm (the OD value at the dominant wavelength of 450 nm minus the OD value at the sub-wavelength of 620/630 nm).

Figure 2:
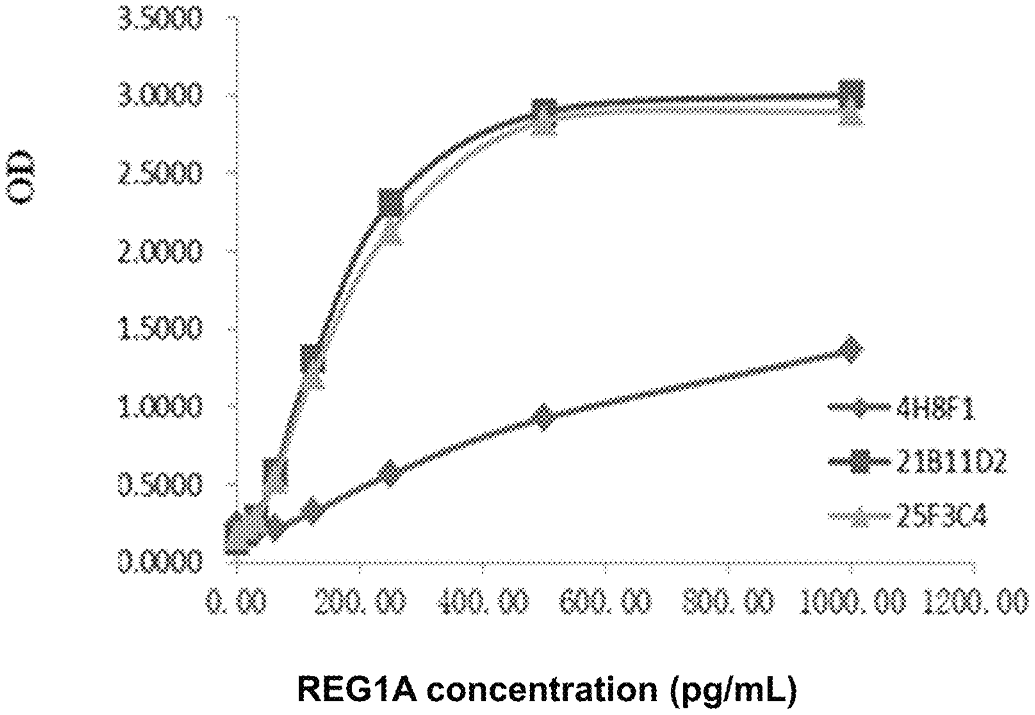
FIG. 2 illustrates the results of antibody pairing and screening.

The results are shown in Table 2 and FIG. 2.

TABLE 2

Results of the Second Pairing Experiment (OD Value)

| Detection antibody | | 12F12A10 | | |
|---|---|---|---|---|
| Coated antibody | | 4H8F1 | 21B11D2 | 25F3C4 |
| REG1A | 1000 | 1.3618 | 3.0054 | 2.9005 |
| pg/mL | 500 | 0.9267 | 2.8918 | 2.8358 |
| | 250 | 0.5655 | 2.3096 | 2.1300 |
| | 125 | 0.3233 | 1.3078 | 1.2050 |
| | 62.5 | 0.2205 | 0.5776 | 0.5386 |
| | 31.25 | 0.1925 | 0.2769 | 0.2784 |
| | 15.625 | 0.2028 | 0.1943 | 0.2411 |
| | 0 | 0.2394 | 0.1382 | 0.1769 |

It can be seen from the results that the antibody pairs—21B11D2-12F12A10 and 25F3C4-12F12A10—show a good linearity within the range that the concentration of REG1A is less than 500 pg/mL, and the antibody pair—4H8F1-12F12A10—shows the optimal linearity when the concentration exceeds 1,000 pg/mL. Considering that the concentration of REG1A in human serum samples is ranges from several ng/ml up to several hundreds or even several thousands ng/ml among various organic gastrointestinal (GI) diseases, the antibody pair—4H8F1-12F12A10—is finally used as the capture and detection antibodies.

(III) Verification of Capture and Detection Antibodies

4H8F1, 21B11D2 and 25F3C4 are used separately used as coated antibodies and 12F12A10 is used as the detection antibody to test serum samples. The steps in "(II) Second pairing and screening" above are followed. When serum samples are tested, antigens are replaced with serum samples that are then added to the wells (100 μL per well) directly. The concentration of proteins in serum samples relative to the standard curve are calculated.

Figure 3:
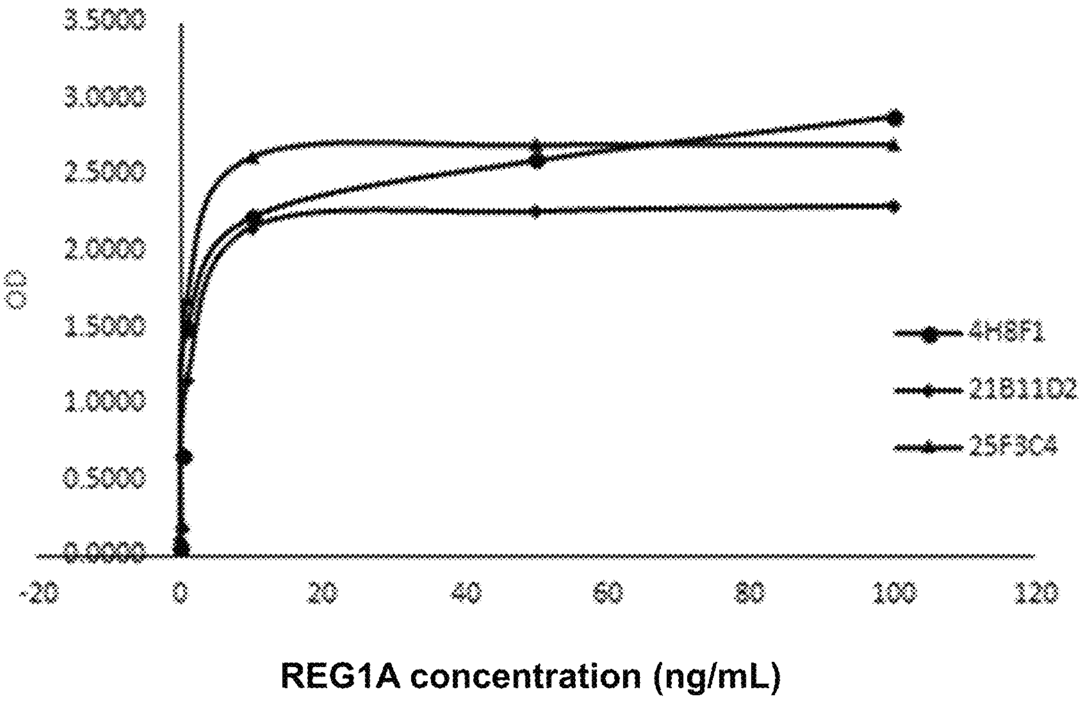
FIG. 3 illustrates the results of antibody pairing and screening.

The results are shown in Table 3 and FIG. 3.

TABLE 3

Results of Serum Detection of REG1A Antibody Pairs

| | Standard | Detection antibody 12F12A10 | | |
|---|---|---|---|---|
| | protein | Coated antibody | | |
| | concentration (ng/ml) | 4H8F1 | 21B11D2 Value | 25F3C4 |
| Standard curve | 100 | 2.8884 | 2.2908 | 2.6976 |
| | 50 | 2.6029 | 2.2536 | 2.6941 |
| | 10 | 2.2273 | 2.1506 | 2.6155 |
| | 1 | 1.4997 | 1.1509 | 1.6932 |
| | 0.1 | 0.6664 | 0.1889 | 0.1995 |
| | 0 | 0.0589 | 0.1013 | 0.0693 |
| | No. | Concentration (ng/ml) | | |
| Serum samples | 170 | 84.0 | 4.1 | 2.3 |
| | 232 | 81.2 | 2.6 | 3.4 |
| | 242 | 43.9 | 2.9 | 6.3 |
| | 253 | 2.8 | 24.9 | 1.1 |

It can be seen from the standard curve that the two antibody pairs—21B11D2-12F12A10 and 25F3C4-12F12A10—show a small change in the OD values when the antigen concentration is equal to or greater than 10 ng/ml, speculating that the antigen-antibody response in this case has reached the saturation point. This point can also be demonstrated by the detection results of serum samples, and for the two antibody pairs, the measured concentrations of proteins in serum samples are not higher than 10 ng/ml. Taking samples 232 and 242 as an example, the measured concentrations of proteins of these two samples—4H8F1-12F12A10—vary greatly, but the concentrations detected of the two antibody pairs—21B11D2-12F12A10 and 25F3C4-12F12A10—show no significant differences.

Embodiment 3 Adoption of the Antibody Pair—4H8F1-12F12A10—for Measurement of REG1A in Different Samples The serum samples are taken from 805 normal cases and the serum samples from 1,924 patients with colorectal cancer (CRC) (including 344 patients with Stage 1 CRC, 669 patients with Stage 2 CRC, 567 patients with Stage 3 CRC and 344 patients with Stage 4 CRC), 89 patients with gastric cancer, 198 patients with adenomatous polyp, 34 patients with IBD, 80 patients with peptic ulcer, 158 patients with gastroenteritis and 7 patients with acute pancreatitis. These serum samples are obtained from Sun Yat-sen University Cancer Center (SYSUCC) and Zhujiang Hospital of Southern Medical University.

As described above, the antibody combination (4H8F1-12F12A10) provided by the present invention is used to test serum samples, and 4H8F1 and 12F12A10 are used as a coated antibody (capture antibody) and a detection antibody respectively to prepare an ELISA kit. Normal cases are used as a control group whose data are compared with the data of the disease group, to conduct a ROC analysis. Then, the results of ROC analysis and the needs of clinical application are combined to determine the cutoff value of concentration of REG1A in human serum as 60 ng/ml, and based on it, the corresponding sensitivity and specificity are calculated. The results are shown in Table 4.

TABLE 4

Detection of the Specificity and Sensitivity of Different Serum Samples (Unit of Protein Concentration: ng/ml)

| Cutoff: 60 | Mean protein concentration | T-test | AUC | P value | Total number of cases | Negative | Positive | Sensitivity | Specificity |
|---|---|---|---|---|---|---|---|---|---|
| Normal cases | 46.42 | | | | 805 | 671 | 134 | | 83.35% |
| CRC 1 | 90.87 | 2.72E−28 | 0.9038 | <0.0001 | 344 | 86 | 258 | 75.00% | |
| CRC 2 | 94.42 | 1.68E−41 | 0.9007 | <0.0001 | 669 | 158 | 511 | 76.38% | |
| CRC 3 | 96.97 | 1.92E−42 | 0.9147 | <0.0001 | 567 | 116 | 451 | 79.54% | |
| CRC 4 | 112.08 | 2.08E−19 | 0.8997 | <0.0001 | 344 | 75 | 269 | 78.20% | |
| CRC ALL | 96.36 | 1.04E−110 | 0.8946 | <0.0001 | 1924 | 477 | 1447 | 75.21% | |
| Gastric cancer | 146.42 | 6.25E−09 | 0.9033 | <0.0001 | 89 | 19 | 70 | 78.65% | |
| Adenomatous polyp | 76.85 | 1.27E−15 | 0.7672 | <0.0001 | 198 | 77 | 121 | 61.11% | |
| IBD | 103.16 | 1.41E−07 | 0.9059 | <0.0001 | 34 | 8 | 26 | 76.47% | |
| Peptic ulcer | 118.33 | 6.55E−10 | 0.8518 | <0.0001 | 80 | 25 | 55 | 68.75% | |
| Gastroenteritis | 102.38 | 3.28E−24 | 0.8705 | <0.0001 | 158 | 39 | 119 | 75.32% | |
| Acute pancreatitis | 334.58 | 3.87E−02 | 0.9807 | <0.0001 | 7 | 0 | 7 | 100.00% | |
| | | Total sensitivity | | | | | | 75.53% | |

Figure 4:
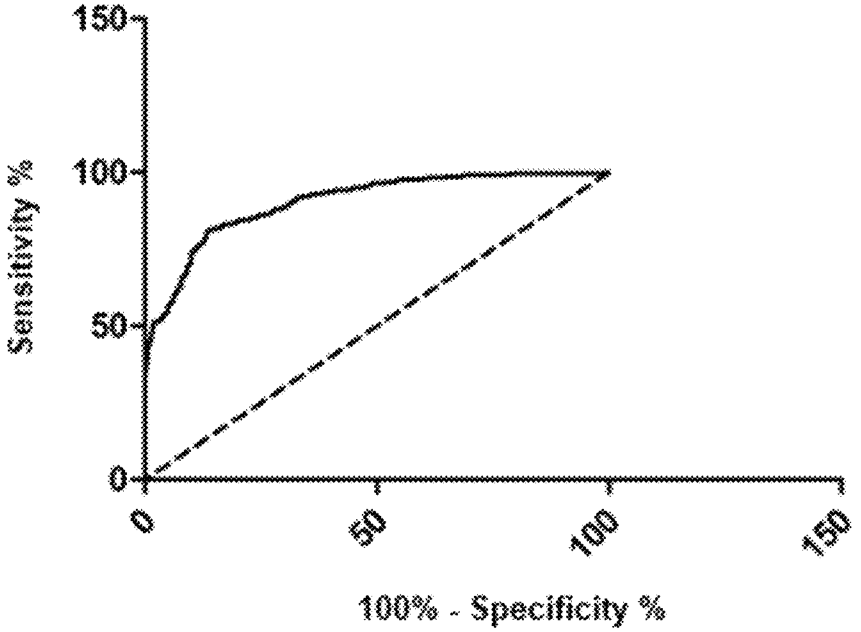
FIG. 4 is a ROC curve drawn according to the detection results of REGIA from serum samples derived from patients with Stage 1 colorectal cancer.

According to the measured data above, GraphPad Prism is used to draw a receiver operating characteristic (ROC) curve, and the results are shown in FIG. 4.

Embodiment 4 Adoption of the Antibody Pair—4H8F1-12F12A10—for Measurement of REG1A in Samples Before and After the Treatment of Patients with Inflammatory Bowel Disease (IBD)

The serum samples of 29 patients with IBD before and after the effective treatment of IBD are obtained from SYSUCC. Infliximab and other monoclonal antibodies or hormones that are often used clinically as a treatment for IBD are used to treat the patients with IBD. The confirmation of treatment efficacy is made by the attending physician according to the endoscopic score. The prevalence situation of patients with IBD is confirmed though enteroscopy, and in the absence of any therapeutic intervention, the serum samples before treatment are obtained. After patients receive medication for 3 months and the treatment is confirmed to be effective, the serum samples after treatment are obtained.

As described above, the antibody combination (4H8F1-12F12A10) provided by the present invention is used to test serum samples, and 4H8F1 and 12F12A10 are used as a coated antibody (capture antibody) and a detection antibody respectively to prepare an ELISA kit, and the concentrations of REG1A in serum samples before and after the effective treatment are tested.

Figure 5:
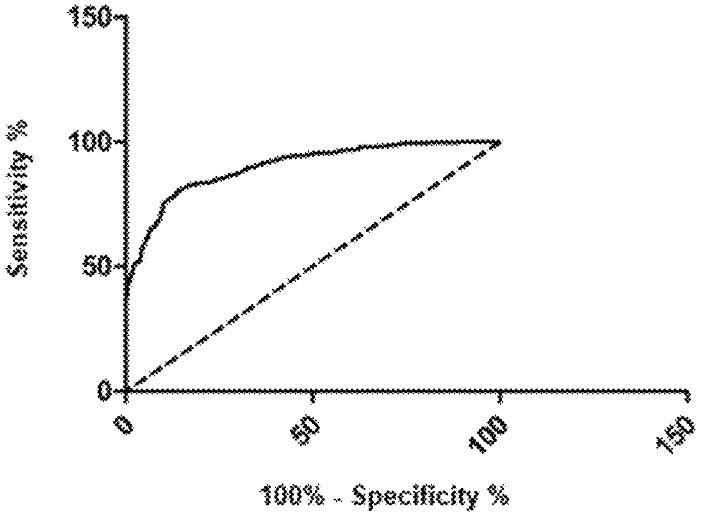
FIG. 5 is a ROC curve drawn according to the detection results of REGIA from serum samples derived from patients with Stage 2 colorectal cancer.
Figure 6:
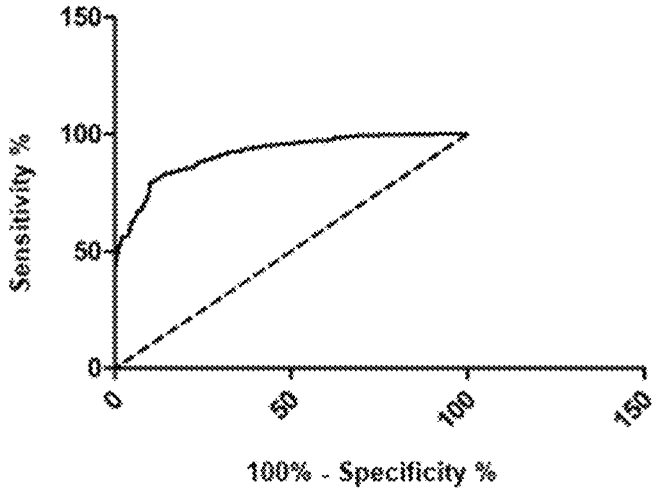
FIG. 6 is a ROC curve drawn according to the detection results of REGIA from serum samples derived from patients with Stage 3 colorectal cancer.
Figure 7:
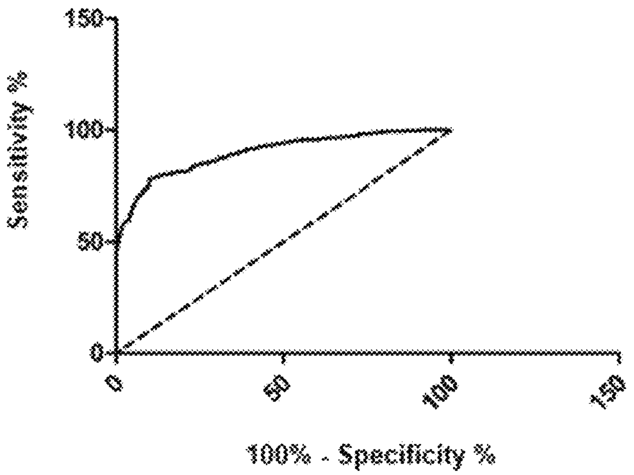
FIG. 7 is a ROC curve drawn according to the detection results of REGIA from serum samples derived from patients with Stage 4 colorectal cancer.
Figure 8:
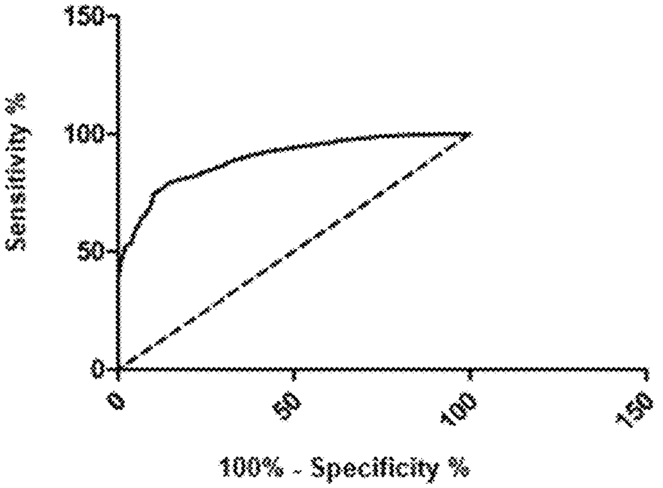
FIG. 8 is a ROC curve drawn according to the detection results of REGIA from serum samples derived from patients with all patients with colorectal cancer.
Figure 9:
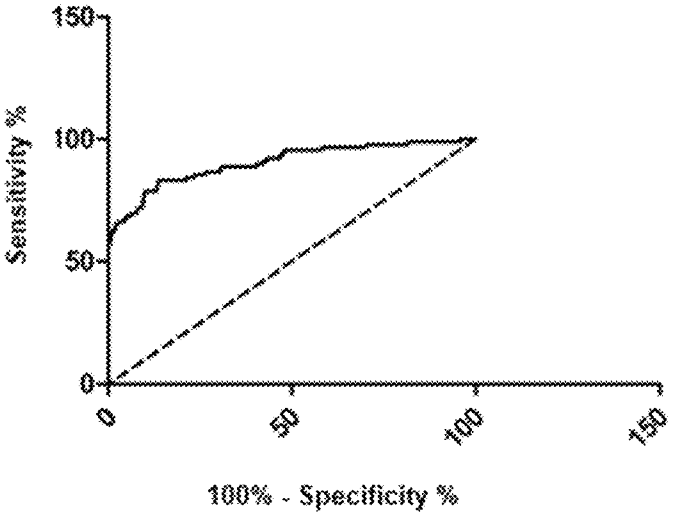
FIG. 9 is a ROC curve drawn according to the detection results of REGIA from serum samples derived from patients with gastric cancer.
Figure 10:
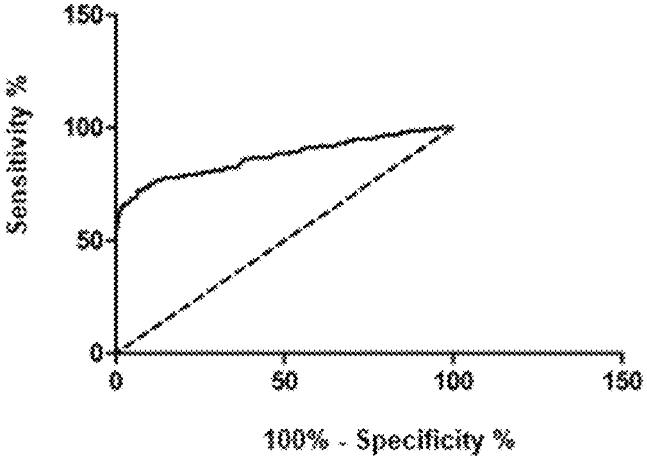
FIG. 10 is a ROC curve drawn according to the detection results of REGIA from serum samples derived from patients with gastroenteritis.
Figure 11:
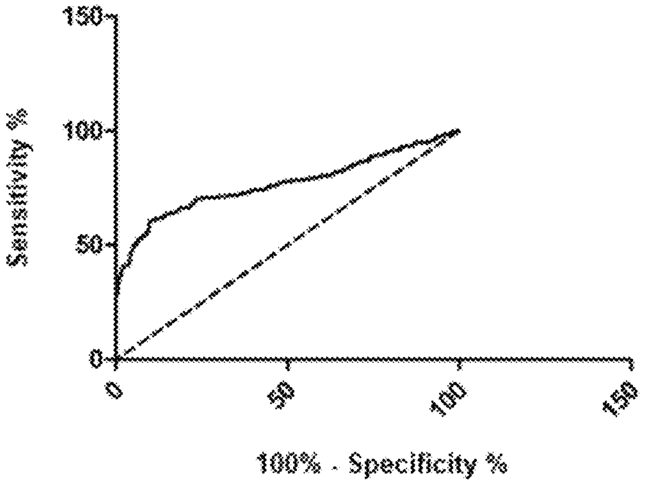
FIG. 11 is a ROC curve drawn according to the detection results of REGIA from serum samples derived from patients with adenomatous polyp.
Figure 12:
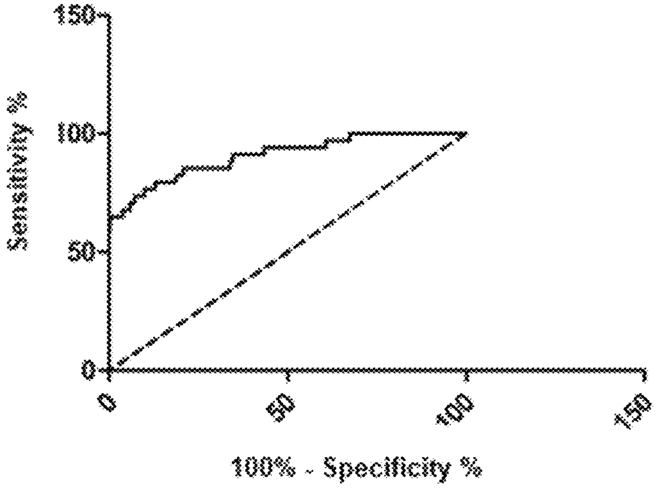
FIG. 12 is a ROC curve drawn according to the detection results of REGIA from serum samples derived from patients with patients with IBD.
Figure 13:
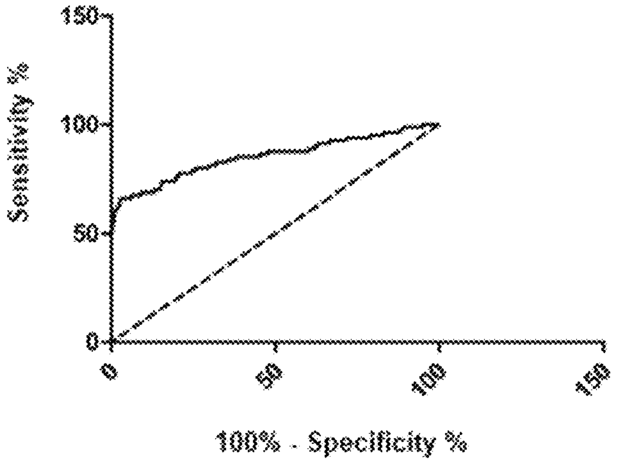
FIG. 13 is a ROC curve drawn according to the detection results of REGIA from serum samples derived from patients with peptic ulcer.
Figure 14:
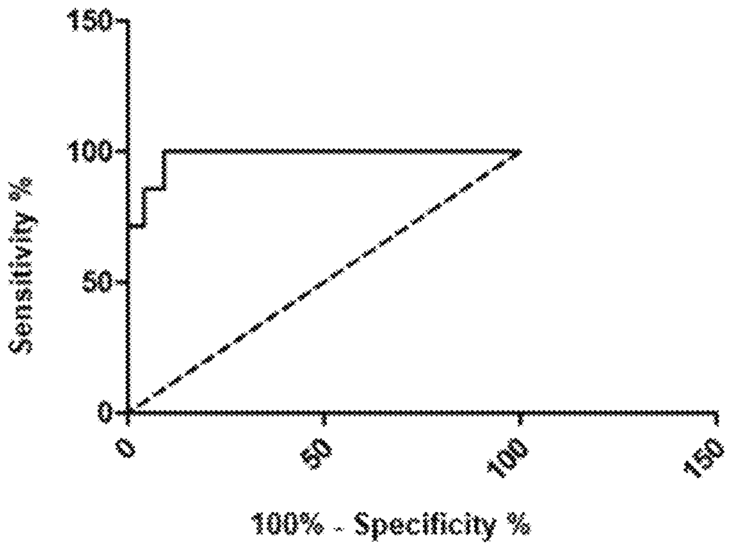
FIG. 14 is a ROC curve drawn according to the detection results of REGIA from serum samples derived from patients with acute pancreatitis.
Figure 15:
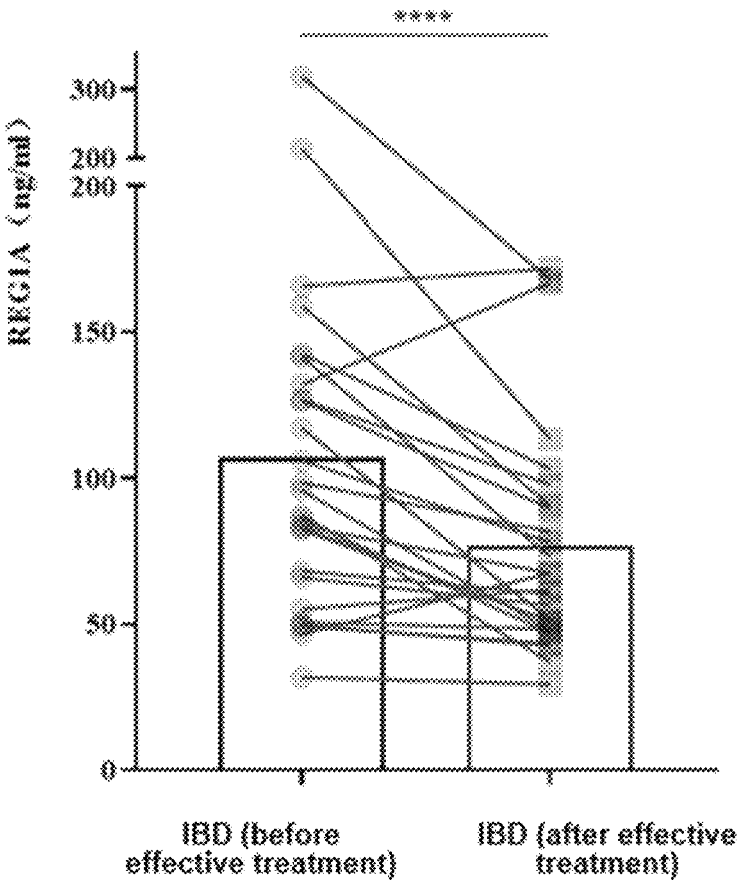
FIG. 15 illustrates the concentrations of REGIA in serum before and after the effective treatment of 29 patients with active IBD (****, P<0.001).

Through the test of the serum samples taken from 29 patients with active IBD, it is found that the concentration of REG1A in serum of 26 patients (89.7%; P<0.0001) after effective treatment is significantly reduced, and the median concentration in serum decreases from 85.86 ng/ml (31.68-317.80) before effective treatment to 60.20 ng/ml (29.34-171.50). For the results, see FIG. 5.

Experiments prove that the antibody pair—4H8F1-12F12A10—provided by the present invention can be used to conduct the companion diagnostics/prognostic monitoring of IBD and help confirm whether the therapeutic drugs for patients with IBD are effective to avoid repeated colonoscopies.

The foregoing description of the preferred embodiments of the present invention is not limited to the present invention. Those skilled in the field may make various changes or deformations according to the present invention, and all changes or deformations are therefore intended to be embraced in the Claims of the present invention, without departing from the spirit thereof.

The invention claimed is:

1. An antibody composition comprising a first antibody and a second antibody, wherein:

the first antibody comprises a first heavy chain and a first light chain;

the first heavy chain comprises a first heavy chain complementarity determining region 1 having the amino acid sequence set forth in SEQ ID NO:1, a first heavy chain complementarity determining region 2 having the amino acid sequence set forth in SEQ ID NO: 2, and a first heavy chain complementarity determining region 3 having the amino acid sequence set forth in SEQ ID NO:3; and the first light chain comprises a first light chain complementarity determining region 1 having the amino acid sequence set forth in SEQ ID NO:6, a first light chain complementarity determining region 2 having the amino acid sequence set forth in SEQ ID NO: 7, and a first light chain complementarity determining region 3 having the amino acid sequence set forth in SEQ ID NO:8;

the second antibody comprises a second heavy chain and a second light chain;

the second heavy chain comprises a second heavy chain complementarity determining region 1 having the amino acid sequence set forth in SEQ ID NO:11, a second heavy chain complementarity determining region 2 having the amino acid sequence set forth in SEQ ID NO:12, and a second heavy chain complementarity determining region 3 having the amino acid sequence set forth in SEQ ID NO:13; and the second light chain comprises a second light chain complementarity determining region 1 having the amino acid sequence set forth in SEQ ID NO:16, a second light chain complementarity determining region 2 having the amino acid sequence set forth in SEQ ID NO: 17, and a second light chain complementarity determining region 3 having the amino acid sequence set forth in SEQ ID NO:18.

2. An antibody combination comprising a first antibody and a second antibody, wherein:

the first antibody comprises a first heavy chain variable region having the amino acid sequence set forth in SEQ ID NO:4 and a first light chain variable region having the amino acid sequence set forth in SEQ ID NO:9; and the second antibody comprises a second heavy chain variable region having the amino acid sequence set forth in SEQ ID NO:14 and a second light chain variable region having the amino acid sequence set forth in SEQ ID NO. 19.

3. The antibody composition according to claim 1, wherein at least one of the first antibody and the second antibody comprises a murine, chimeric, or humanized antibody.

4. The antibody composition according to claim 1, wherein at least one of the first antibody and the second antibody comprises a monoclonal antibody, an Fab fragment, an Fv fragment, or an scFv.

5. The antibody composition according to claim 4, wherein each of the first antibody and the second antibody comprises a monoclonal antibody.

6. The antibody composition according to claim 5, wherein:

each of the first antibody and the second antibody comprises a mouse IgG1 monoclonal antibody; and the mouse IgG1 monoclonal antibody comprises a kappa light chain.

7. The antibody composition according to claim 2, wherein:

the first heavy chain variable region is disposed within a first heavy chain;

the first heavy chain has the amino acid sequence set forth in SEQ ID NO:5;

the first light chain variable region is disposed within a first light chain;

the first light chain has the amino acid sequence set forth in SEQ ID NO:10;

the second heavy chain variable region is disposed within a second heavy chain;

the second heavy chain has the amino acid sequence set forth in SEQ ID NO:15;

the second light chain variable region is disposed within a second light chain; and the second light chain has the amino acid sequence set forth in SEQ ID NO:20.

8. The antibody composition according to claim 1, wherein at least one of the first antibody and the second antibody further comprises a detectable label.

9. The antibody combination according to claim 8, wherein the second antibody comprises a detectable label.

10. The antibody combination according to claim 9, wherein the detectable label comprises an enzyme label, a radioactive label, a luminescent label, a color-rendering label, a hapten, a metal complex, or a metal.

11. A kit comprising the antibody composition according to claim 1.

12. The kit according to claim 11, wherein the second antibody comprises a detectable label.

13. The kit according to claim 12, wherein the detectable label comprises an enzyme label, a radioactive label, a luminescent label, a color-rendering label, a hapten, a metal complex, or a metal.

14. The kit according to claim 11, wherein the kit further comprises an antibody diluent, a wash buffer, a blocking buffer, a diluent, an immunosorbent plate, a color-developing agent, and a stop buffer.

15. A method for detecting a Regenerating Islet-Derived Protein 1α (REG1α) protein, the method comprising contacting a REG1α protein with a first antibody and a second antibody, wherein:

the first antibody comprises a first heavy chain and a first light chain;

the first heavy chain comprises a first heavy chain complementarity determining region 1 having the amino acid sequence set forth in SEQ ID NO:1, a first heavy chain complementarity determining region 2 having the amino acid sequence set forth in SEQ ID NO: 2, and a first heavy chain complementarity determining region 3 having the amino acid sequence set forth in SEQ ID NO:3; and the first light chain comprises a first light chain complementarity determining region 1 having the amino acid sequence set forth in SEQ ID NO:6, a first light chain complementarity determining region 2 having the amino acid sequence set forth in SEQ ID NO: 7, and a first light chain complementarity determining region 3 having the amino acid sequence set forth in SEQ ID NO:8;

the second antibody comprises a second heavy chain and a second light chain;

the second heavy chain comprises a second heavy chain complementarity determining region 1 having the amino acid sequence set forth in SEQ ID NO:11, a second heavy chain complementarity determining region 2 having the amino acid sequence set forth in SEQ ID NO:12, and a second heavy chain complementarity determining region 3 having the amino acid sequence set forth in SEQ ID NO: 13;

the second light chain comprises a second light chain complementarity determining region 1 having the amino acid sequence set forth in SEQ ID NO:16, a second light chain complementarity determining region 2 having the amino acid sequence set forth in SEQ ID NO: 17, and a second light chain complementarity determining region 3 having the amino acid sequence set forth in SEQ ID NO: 18; and the REG1α protein is present within a biological sample obtained from a subject.

* * * * *

SEQUENCE LISTING

```
Sequence total quantity: 26
SEQ ID NO: 1            moltype = AA  length = 7
FEATURE                 Location/Qualifiers
source                  1..7
                        mol_type = protein
                        organism = Mus musculus
SEQUENCE: 1
TSGMSVG                                                                   7

SEQ ID NO: 2            moltype = AA  length = 16
FEATURE                 Location/Qualifiers
source                  1..16
                        mol_type = protein
                        organism = Mus musculus
SEQUENCE: 2
HIWWNDDKFY NPALKS                                                         16

SEQ ID NO: 3            moltype = AA  length = 8
FEATURE                 Location/Qualifiers
source                  1..8
                        mol_type = protein
                        organism = Mus musculus
SEQUENCE: 3
IEEGWFAY                                                                  8
```

```
SEQ ID NO: 4            moltype = AA  length = 118
FEATURE                 Location/Qualifiers
source                  1..118
                        mol_type = protein
                        organism = Mus musculus
SEQUENCE: 4
QVTLKESGPG ILQPSQTLSL TCSFSGFSLS TSGMSVGWIR QPSGKGLEWL AHIWWNDDKF  60
YNPALKSRLT ISKDTSKNQI FLKIASVVTA DSATYYCARI EEGWFAYWGQ GTLVTVST    118

SEQ ID NO: 5            moltype = AA  length = 442
FEATURE                 Location/Qualifiers
source                  1..442
                        mol_type = protein
                        organism = Mus musculus
SEQUENCE: 5
QVTLKESGPG ILQPSQTLSL TCSFSGFSLS TSGMSVGWIR QPSGKGLEWL AHIWWNDDKF  60
YNPALKSRLT ISKDTSKNQI FLKIASVVTA DSATYYCARI EEGWFAYWGQ GTLVTVSTAK  120
TTPPSVYPLA PGSAAQTNSM VTLGCLVKGY FPEPVTVTWN SGSLSSGVHT FPAVLQSDLY  180
TLSSSVTVPS STWPSETVTC NVAHPASSTK VDKKIVPRDC GCKPCICTVP EVSSVFIFPP  240
KPKDVLTITL TPKVTCVVVD ISKDDPEVQF SWFVDDVEVH TAQTQPREEQ FNSTFRSVSE  300
LPIMHQDWLN GKEFKCRVNS AAFPAPIEKT ISKTKGRPKA PQVYTIPPPK EQMAKDKVSL  360
TCMITDFFPE DITVEWQWNG QPAENYKNTQ PIMDTDGSYF VYSKLNVQKS NWEAGNTFTC  420
SVLHEGLHNH HTEKSLSHSP GK                                          442

SEQ ID NO: 6            moltype = AA  length = 11
FEATURE                 Location/Qualifiers
source                  1..11
                        mol_type = protein
                        organism = Mus musculus
SEQUENCE: 6
KASQTMSNDV A                                                      11

SEQ ID NO: 7            moltype = AA  length = 7
FEATURE                 Location/Qualifiers
source                  1..7
                        mol_type = protein
                        organism = Mus musculus
SEQUENCE: 7
YASNRYT                                                           7

SEQ ID NO: 8            moltype = AA  length = 9
FEATURE                 Location/Qualifiers
source                  1..9
                        mol_type = protein
                        organism = Mus musculus
SEQUENCE: 8
QQDYSSPLT                                                         9

SEQ ID NO: 9            moltype = AA  length = 107
FEATURE                 Location/Qualifiers
source                  1..107
                        mol_type = protein
                        organism = Mus musculus
SEQUENCE: 9
SIVMTQTPKF LLVSVGDRVT ITCKASQTMS NDVAWYQQKP GQSPKLLIYY ASNRYTGVPD  60
RFTGSGYGTD FTFTISTVQA EDLAVYFCQQ DYSSPLTFGA GTKLELK               107

SEQ ID NO: 10           moltype = AA  length = 214
FEATURE                 Location/Qualifiers
source                  1..214
                        mol_type = protein
                        organism = Mus musculus
SEQUENCE: 10
SIVMTQTPKF LLVSVGDRVT ITCKASQTMS NDVAWYQQKP GQSPKLLIYY ASNRYTGVPD  60
RFTGSGYGTD FTFTISTVQA EDLAVYFCQQ DYSSPLTFGA GTKLELKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 11           moltype = AA  length = 5
FEATURE                 Location/Qualifiers
source                  1..5
                        mol_type = protein
                        organism = Mus musculus
SEQUENCE: 11
SYMMH                                                             5

SEQ ID NO: 12           moltype = AA  length = 17
FEATURE                 Location/Qualifiers
```

-continued

```
source                  1..17
                        mol_type = protein
                        organism = Mus musculus
SEQUENCE: 12
YINPSSGYTD YNQKFKD                                          17

SEQ ID NO: 13           moltype = AA  length = 9
FEATURE                 Location/Qualifiers
source                  1..9
                        mol_type = protein
                        organism = Mus musculus
SEQUENCE: 13
YRYPHYFDY                                                   9

SEQ ID NO: 14           moltype = AA  length = 118
FEATURE                 Location/Qualifiers
source                  1..118
                        mol_type = protein
                        organism = Mus musculus
SEQUENCE: 14
QVQLQQSATE LARPGASVKM SCKASGYTFT SYMMHWVKQR PGQGLEWIGY INPSSGYTDY  60
NQKFKDKTTL TADKSSSTAY MQLSSLTSED SAVYYCARYR YPHYFDYWGQ GTTLTVSS    118

SEQ ID NO: 15           moltype = AA  length = 442
FEATURE                 Location/Qualifiers
source                  1..442
                        mol_type = protein
                        organism = Mus musculus
SEQUENCE: 15
QVQLQQSATE LARPGASVKM SCKASGYTFT SYMMHWVKQR PGQGLEWIGY INPSSGYTDY  60
NQKFKDKTTL TADKSSSTAY MQLSSLTSED SAVYYCARYR YPHYFDYWGQ GTTLTVSSAK  120
TTPPSVYPLA PGSAAQTNSM VTLGCLVKGY FPEPVTVTWN SGSLSSGVHT FPAVLQSDLY  180
TLSSSVTVPS STWPSETVTC NVAHPASSTK VDKKIVPRDC GCKPCICTVP EVSSVFIFPP  240
KPKDVLTITL TPKVTCVVVD ISKDDPEVQF SWFVDDVEVH TAQTQPREEQ FNSTFRSVSE  300
LPIMHQDWLN GKEFKCRVNS AAFPAPIEKT ISKTKGRPKA PQVYTIPPPK EQMAKDKVSL  360
TCMITDFFPE DITVEWQWNG QPAENYKNTQ PIMDTDGSYF VYSKLNVQKS NWEAGNTFTC  420
SVLHEGLHNH HTEKSLSHSP GK                                          442

SEQ ID NO: 16           moltype = AA  length = 10
FEATURE                 Location/Qualifiers
source                  1..10
                        mol_type = protein
                        organism = Mus musculus
SEQUENCE: 16
SASSSVSYIH                                                  10

SEQ ID NO: 17           moltype = AA  length = 7
FEATURE                 Location/Qualifiers
source                  1..7
                        mol_type = protein
                        organism = Mus musculus
SEQUENCE: 17
DTSKLAS                                                     7

SEQ ID NO: 18           moltype = AA  length = 9
FEATURE                 Location/Qualifiers
source                  1..9
                        mol_type = protein
                        organism = Mus musculus
SEQUENCE: 18
QQWSSNPPT                                                   9

SEQ ID NO: 19           moltype = AA  length = 106
FEATURE                 Location/Qualifiers
source                  1..106
                        mol_type = protein
                        organism = Mus musculus
SEQUENCE: 19
QIVLTQSPAI MSASPGEKVT MTCSASSSVS YIHWYQQKSG TSPKRWIYDT SKLASGVPAR  60
FSGSGSGTSY SLTISSMEAE DAAIYYCQQW SSNPPTFGAG TKLELK                 106

SEQ ID NO: 20           moltype = AA  length = 213
FEATURE                 Location/Qualifiers
source                  1..213
                        mol_type = protein
                        organism = Mus musculus
SEQUENCE: 20
QIVLTQSPAI MSASPGEKVT MTCSASSSVS YIHWYQQKSG TSPKRWIYDT SKLASGVPAR  60
FSGSGSGTSY SLTISSMEAE DAAIYYCQQW SSNPPTFGAG TKLELKRADA APTVSIFPPS  120
```

-continued

```
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                               213

SEQ ID NO: 21          moltype = AA  length = 450
FEATURE                Location/Qualifiers
source                 1..450
                       mol_type = protein
                       organism = Mus musculus
SEQUENCE: 21
DVKLVESGGG LVKPGGSLKL SCAASGFTFS SFSMSWFRQT PDKRLEWVAT ISSGGSSTYY  60
PDSVKGRFTI SRDNAKNTLY LQMTSLKSED TAIFYCRGGY YGNYDPLDYW GQGTSVTVSA  120
AKTTAPSVYP LAPVCGDTTG SSVTLGCLVK GYFPEPVTLT WNSGSLSSGV HTFPAVLQSD  180
LYTLSSSVTV TSSTWPSQSI TCNVAHPASS TKVDKKIEPR GPTIKPCPPC KCPAPNLLGG  240
PSVFIFPPKI KDVLMISLSP IVTCVVVDVS EDDPDVQISW FVNNVEVHTA QTQTHREDYN  300
STLRVVSALP IQHQDWMSGK EFKCKVNNKD LPAPIERTIS KPKGSVRAPQ VYVLPPPEEE  360
MTKKQVTLTC MVTDFMPEDI YVEWTNNGKT ELNYKNTEPV LDSDGSYFMY SKLRVEKKNW  420
VERNSYSCSV VHEGLHNHHT TKSFSRTPGK                                   450

SEQ ID NO: 22          moltype = AA  length = 214
FEATURE                Location/Qualifiers
source                 1..214
                       mol_type = protein
                       organism = Mus musculus
SEQUENCE: 22
DIVMIQSQKF MSTSVGDRVS ITCTASHNVD SNVAWYQQKP GQSPQALIYS ASYRYSGVPD  60
RFTGSGSGTD FTLTINNVQS EDLAEYFCQQ YNSYPLTFGG GTRLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 23          moltype = AA  length = 453
FEATURE                Location/Qualifiers
source                 1..453
                       mol_type = protein
                       organism = Mus musculus
SEQUENCE: 23
QAQLQQSGAE LVRPGASVTL SCKASGYIFT DYEMHWVKQT PVHGLEWIGA IDPETGGTAY  60
NQKFKGKARL TADKSSSTAY MELRSLTSED SAVYYCTIYY TNHFDYWGQG TTLTVSSAKT  120
TPPSVYPLAP GCGDTTGSSV TLGCLVKGYF PESVTVTWNS GSLSSSVHTF PALLQSGLYT  180
MSSSVTVPSS TWPSQTVTCS VAHPASSTTV DKKLEPSGPI STINPCPPCK ECHKCPAPNL  240
EGGPSVFIFP PNIKDVLMIS LTPKVTCVVV DVSEDDPDVR ISWFVNNVEV HTAQTQTHRE  300
DYNSTIRVVS ALPIQHQDWM SGKEFKCKVN NKDLPSPIER TISKIKGLVR APQVYILPPP  360
AEQLSRKDVS LTCLVVGFNP GDISVEWTSN GHTEENYKDT APVLDSDGSY FIYSKLDIKT  420
SKWEKTDSFS CNVRHEGLKN YYLKKTISRS PGK                               453

SEQ ID NO: 24          moltype = AA  length = 219
FEATURE                Location/Qualifiers
source                 1..219
                       mol_type = protein
                       organism = Mus musculus
SEQUENCE: 24
DVVMTQTPLS LPVSLGDQAS ISCRSSQSLV YSNGDTYLYW YLQKPGQSPK LLIYKVSNRF  60
SGVPDRFSGS GSGTDFTLKI SRVEAEDLGV YFCSQSTHVP LTFGAGTKLE LKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                         219

SEQ ID NO: 25          moltype = AA  length = 453
FEATURE                Location/Qualifiers
source                 1..453
                       mol_type = protein
                       organism = Mus musculus
SEQUENCE: 25
QVQLQQSGAE LVRPGASVTL SCKASGYTFT DYEVHWVKQT PVHGLEWIGA IDPETGGTAY  60
NLKFKGKAIL TADKSSSTAY MELRSLTSED SAVYYFTIYY TNNFDYWGQG TALTVSSAKT  120
TPPSVYPLAP GCGDTTGSSV TLGCLVKGYF PESVTVTWNS GSLSSSVHTF PALLQSGLYT  180
MSSSVTVPSS TWPSQTVTCS VAHPASSTTV DKKLEPSGPI STINPCPPCK ECHKCPAPNL  240
EGGPSVFIFP PNIKDVLMIS LTPKVTCVVV DVSEDDPDVR ISWFVNNVEV HTAQTQTHRE  300
DYNSTIRVVS ALPIQHQDWM SGKEFKCKVN NKDLPSPIER TISKIKGLVR APQVYILPPP  360
AEQLSRKDVS LTCLVVGFNP GDISVEWTSN GHTEENYKDT APVLDSDGSY FIYSKLDIKT  420
SKWEKTDSFS CNVRHEGLKN YYLKKTISRS PGK                               453

SEQ ID NO: 26          moltype = AA  length = 219
FEATURE                Location/Qualifiers
source                 1..219
                       mol_type = protein
                       organism = Mus musculus
```

-continued

```
SEQUENCE: 26
DVVMTQTPLS LPVSLGDQAS ISCRSSQSLV YSDGNTYLHW YLQKPGQSPK LLIYKVSYRF  60
SGVPDRFSGS GSGTDFTLKI SRVEAEDLGV YFCSQSTHVP LTFGAGTKLE LKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                        219
```